United States Patent
Emoto

(10) Patent No.: US 6,995,386 B2
(45) Date of Patent: *Feb. 7, 2006

(54) FLUORESCENCE DETECTING DEVICE WITH INTEGRATED CIRCUIT AND PHOTODIODE, AND DETECTION METHOD

(75) Inventor: Fumiaki Emoto, Hirakata (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/962,239

(22) Filed: Oct. 8, 2004

(65) Prior Publication Data

US 2005/0051744 A1    Mar. 10, 2005

Related U.S. Application Data

(62) Division of application No. 10/154,095, filed on May 22, 2002, now Pat. No. 6,844,563.

(30) Foreign Application Priority Data

May 22, 2001 (JP) ............................. 2001-152929
May 22, 2001 (JP) ............................. 2001-152931

(51) Int. Cl.
    *G01N 21/64*    (2006.01)
(52) U.S. Cl. .................. 250/576; 250/226; 250/373; 356/417; 422/82.07; 422/82.06
(58) Field of Classification Search ............ 250/214.1, 250/461.1, 461.2, 372, 373, 226, 458.1; 356/311, 356/317, 318, 410, 411, 417; 422/82.06–82.08
See application file for complete search history.

(56) References Cited

U.S. PATENT DOCUMENTS

| 4,755,667 A | * | 7/1988 | Marsoner et al. ...... 250/227.24 |
| 4,833,332 A | | 5/1989 | Robertson et al. ....... 250/458.1 |
| 4,861,163 A | | 8/1989 | Bach .......................... 356/417 |
| 5,355,215 A | * | 10/1994 | Schroeder et al. .......... 356/317 |
| 5,370,842 A | | 12/1994 | Miyazaki et al. ......... 422/82.06 |
| 5,667,656 A | | 9/1997 | Kambara .................... 204/603 |
| 5,894,351 A | | 4/1999 | Colvin ....................... 356/417 |
| 6,117,643 A | | 9/2000 | Simpson et al. ............. 435/7.1 |
| 6,330,464 B1 | * | 12/2001 | Colvin et al. ............... 600/316 |
| 2003/0156290 A1 | * | 8/2003 | Colvin et al. ............... 356/411 |

FOREIGN PATENT DOCUMENTS

| EP | 0 601 714 | 6/1994 |
| JP | 6-148076 | 5/1994 |
| JP | 7-83900 | 3/1995 |

* cited by examiner

*Primary Examiner*—David Porta
*Assistant Examiner*—Stephen Yam
(74) *Attorney, Agent, or Firm*—Hamre, Schumann, Mueller & Larson P.C.

(57) ABSTRACT

A fluorescence detecting device is configured so that a semiconductor integrated circuit substrate includes a photodiode and a signal detecting circuit for detecting charges obtained as a result of photoelectric conversion by the photodiode, and a fluorescence reaction vessel where a fluorescence reaction occurs is arranged above the foregoing photodiode. Furthermore, in the device, an excitation-light-entry preventing layer is provided at one or more of a surface portion of the photodiode and a position between the photodiode and the fluorescence reaction vessel.

8 Claims, 11 Drawing Sheets

FLUORESCENCE DETECTING DEVICE WITH INTEGRATED CIRCUIT AND PHOTODIODE, AND DETECTION METHOD

This application is a Division of application Ser. No. 10/154,095, now U.S. Pat. No. 6,844,563 filed May 22, 2002, which patent is incorporated herein by reference.

BACKGROUND OF THE INVENTION

1. Field of the Invention

The present invention relates generally to a fluorescence detecting device for detecting a fluorescence reaction, for instance, a fluorescence detecting device suitable for detection, etc., of a specific gene contained in a sample.

2. Related Background Art

Recently, the genome sequence analysis has been developed significantly, and the determination of the whole base-sequence of the human genome will be completed in 2003. Besides, the determination of genomes of other creatures is proceeding throughout the world. With this development of the genome analysis, the detection of genes has an increased significance from the viewpoint of the determination of functions of genes, the medical diagnosis, etc. Examples of conventional gene detecting methods include the gene amplification methods represented by the polymerase chain reaction (PCR) method, while recently the gene detecting method employing DNA chips is used widely.

A DNA chip is an approximately 1 cm×1 cm glass chip, silicon chip, etc. on which a plurality of single-strand DNAs are fixed. Examples of the single-strand DNAs to be fixed include DNAs as etiologic genes. The gene analysis employing a DNA chip is performed, for instance, in the following manner. First of all, a target gene is extracted from cells (for instance, blood cells). Then, the target gene is amplified by the PCR method. In the amplification, a fluorescent substance is employed to label an amplification product. A DNA chip is immersed in a solution containing nucleic acid strands labeled with the fluorescent dye, so that hybridization occurs. Thereafter, the DNA chip is washed so that nucleic acids that have not been hybridized are removed.

Subsequently, the DNA chip is irradiated with an excitation light, and the fluorescence is detected. An example of a fluorescence detecting device used herein is shown in FIG. 11. In the device, an excitation light 309 from a light source 305 such as a laser is reflected by a beam splitter 304, and enters an objective lens 306, where the light is focused so as to be incident on a fixed portion 307 of a nucleic acid probe on a DNA chip 308. In the case where a double strand is formed as a result of hybridization, a fluorescent substance is present on the DNA chip 308, and therefore, a fluorescence 310 is emitted upon the irradiation by the excitation light 309. Normally, the fluorescence 310 and the excitation light 309 have a wavelength difference on the order of several tens of nanometers. A part 311 of the fluorescence and a reflected light of the excitation light 309 return to the objective lens, and reach the beam splitter 304. Most of the reflected light of the excitation light 309 is reflected by the beam splitter 304, thereby being directed to the light source side. The part 311 of the fluorescence passes through the beam splitter 204, thereby being directed to a photodetector 301. The part 311 of the fluorescence that has passed through the beam splitter 304 passes through a filter 303 that limits a wavelength, while the reflected light of the excitation light 309 is blocked by the same. Furthermore, the part 311 of the fluorescence passes through a photodetector lens 302 and enters the photodetector 301 for measuring an intensity of the fluorescence, where the fluorescence is detected.

However, the above-described conventional fluorescence detecting device is a large-scale and complex device having a long optical path, through which the fluorescence is lost partly, thereby leading to a problem of low detection sensitivity.

SUMMARY OF THE INVENTION

Therefore, with the foregoing in mind, it is an object of the present invention to provide a fluorescence detecting device that is small in size and has a high sensitivity.

To achieve the foregoing object, a first fluorescence detecting device of the present invention includes a semiconductor integrated circuit substrate including a photodiode and a signal detecting circuit for detecting charges obtained as a result of photoelectric conversion by the photodiode, and a fluorescence reaction vessel where a fluorescence reaction occurs, which is arranged above the photodiode. Here, the fluorescence reaction vessel may be displaced from a position immediately above the photodiode as long as at least a part of the fluorescence generated in the fluorescence reaction vessel enters the photodiode. Normally, at least a part of the fluorescence reaction vessel is positioned above the photodiode. In the foregoing device, an excitation-light-entry preventing layer is formed one or more of a surface portion of the photodiode and a position between the photodiode and the fluorescence reaction vessel.

Thus, in the fluorescence detecting device of the present invention, the fluorescence reaction vessel is arranged above the photodiode that detects a fluorescence. This makes an optical path shorter in length, thereby ensuring the improvement of the fluorescence detecting sensitivity and the reduction of the overall size of the device. Furthermore, since this device includes an excitation-light-entry preventing layer, the excitation light is prevented from entering the photodiode. Therefore, it is possible to eliminate influences of the excitation light. It should be noted that the excitation light entry preventing layer is defined as a layer that prevents at least a part of the excitation light from entering the photodiode. Therefore, even if a layer slightly transmits the excitation light, it is acceptable as the excitation light entry preventing layer.

The first device may be configured so that the photodiode includes a high-concentration first-conductivity-type semiconductor layer, a second-conductivity-type semiconductor layer, and a low-concentration first-conductivity-type semiconductor layer that are laminated in the stated order from a surface side of the photodiode, wherein, when a reverse bias is applied, a part of the high-concentration first-conductivity-type semiconductor layer is not depleted, and the second-conductivity-type semiconductor layer is depleted, and the high-concentration first-conductivity-type semiconductor layer constitutes the excitation-light-entry preventing layer. The excitation light has a wavelength shorter than that of a fluorescence and hence is converted by the photoelectric conversion in a surface portion of the photodiode. Therefore, the foregoing configuration prevents charges generated from the excitation light in the vicinity of the surface portion from being accumulated in the photodiode.

Furthermore, in the first device, the excitation-light-entry preventing layer may be a light absorbing layer that absorbs an excitation light and is arranged between the photodiode and the fluorescence reaction vessel. Alternatively, the excitation-light-entry preventing layer may be a light interference layer that reflects an excitation light arranged between the photodiode and the fluorescence reaction vessel. Further alternatively, the excitation-light-entry preventing layer may be a gas layer arranged between the photodiode and the fluorescence reaction vessel, and an excitation light is set so as to be incident in a direction such that the excitation light is reflected totally at an interface between the gas layer and a bottom face of the fluorescence reaction vessel, where the refractive index decreases.

Furthermore, in the first device, a single-strand DNA may be fixed on an internal bottom face of the fluorescence reaction vessel. In this case, it is used as a DNA chip. Alternatively, an antibody or an antigen may be fixed on an internal bottom face of the fluorescence reaction vessel. Furthermore, in the foregoing fluorescence reaction vessel, a gene amplification reaction such as the PCR may be carried out so that an amplification product should be detected by fluorescence.

To achieve the aforementioned object, a second fluorescence detecting device of the present invention includes a semiconductor integrated circuit substrate including a first photodiode, a second photodiode, and a signal detecting circuit for detecting electric signals from the photodiodes, a fluorescence reaction vessel where a fluorescence reaction occurs, and a first optical filter and a second optical filter that have different light transmission spectral characteristics from each other. In the device, the first optical filter is arranged above the first photodiode, the second optical filter is arranged above the second photodiode, and the fluorescence reaction vessel is formed above these optical filters, and the signal detecting circuit outputs a fluorescence signal from which influences of an excitation light are eliminated. The fluorescence signal is derived based on a difference between the optical filters as to the ratio of the fluorescence signal to an excitation light signal, which difference depends on a difference between the light transmission spectral characteristics.

Thus, in the fluorescence detecting device of the present invention, the fluorescence reaction vessel is arranged above the photodiode that detects a fluorescence. This makes an optical path shorter in length, thereby ensuring the improvement of the fluorescence detecting sensitivity and the reduction of the overall size of the device. Furthermore, in the foregoing device, a fluorescence signal is derived based on a difference between the optical filters as to the ratio of the fluorescence signal to an excitation light signal, according to a difference between the light transmission spectral characteristics, with influences of an excitation light being eliminated therefrom. Therefore, it is possible to achieve the fluorescence detection with high precision.

In the second device, one detection unit preferably is composed of the first photodiode and the first optical filter, plus the second photodiode and the second optical filter, and the device preferably includes a plurality of the detection units. This configuration allows the detection units to perform different tests, respectively.

Furthermore, in the second device, color filters having different colors from each other preferably are used as these optical filters.

Furthermore, in the second device, a single-strand DNA may be fixed on an internal bottom face of the fluorescence reaction vessel. In this case, it is used as a DNA chip. Alternatively, an antibody or an antigen may be fixed on an internal bottom face of the fluorescence reaction vessel. Furthermore, in the foregoing fluorescence reaction vessel, a gene amplification reaction such as the PCR may be carried out so that an amplification product should be detected by fluorescence.

DETAILED DESCRIPTION OF THE INVENTION

First Embodiment

Figure 1:
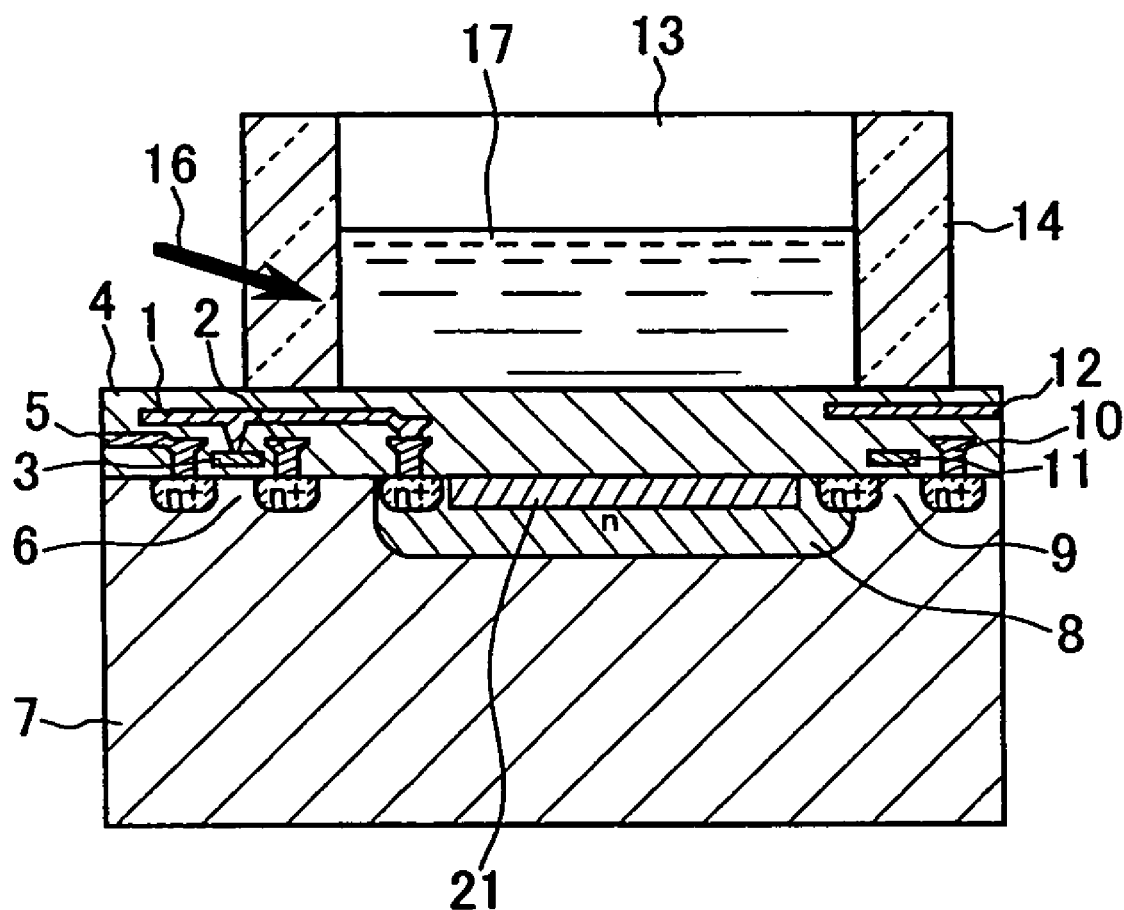
FIG. 1 is a cross-sectional view illustrating an example of a first fluorescence detecting device of the present invention.
Figure 2A:
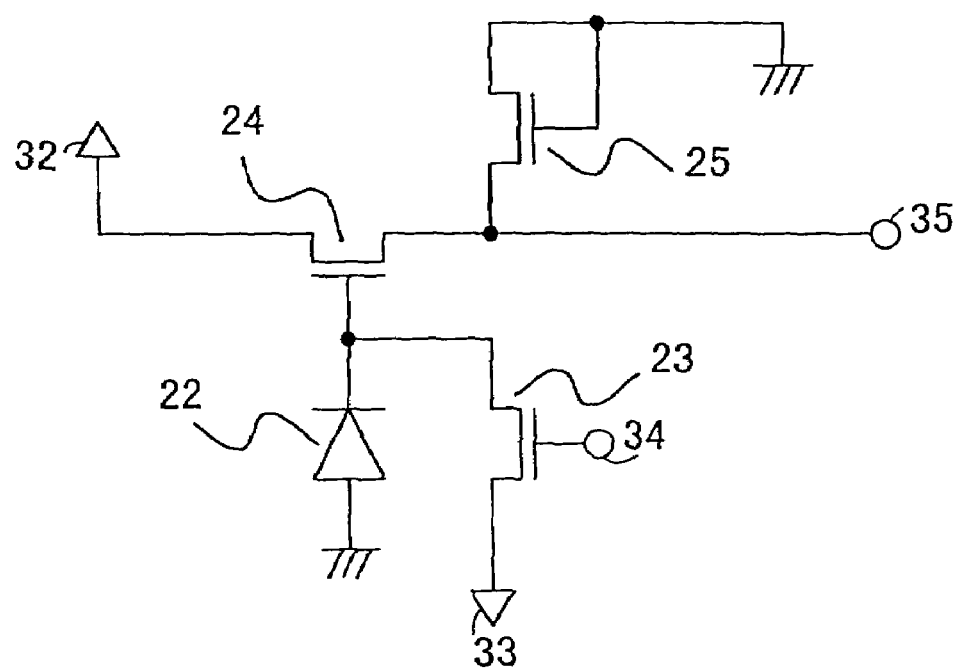
FIG. 2A is a circuit diagram of the device shown in FIG. 1.
Figure 2B:
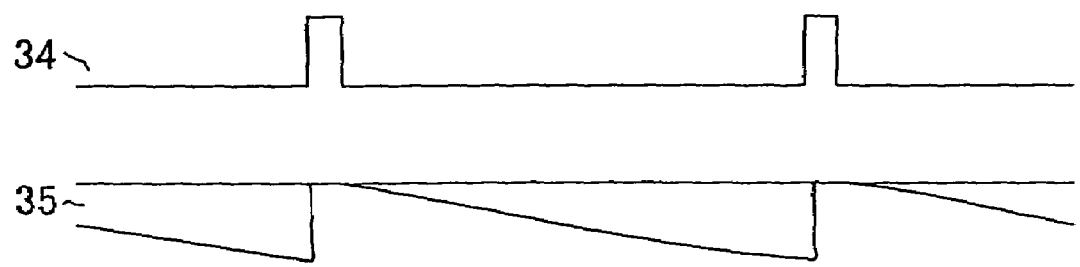
FIG. 2B is a driving timing chart of the same.
Figure 3:
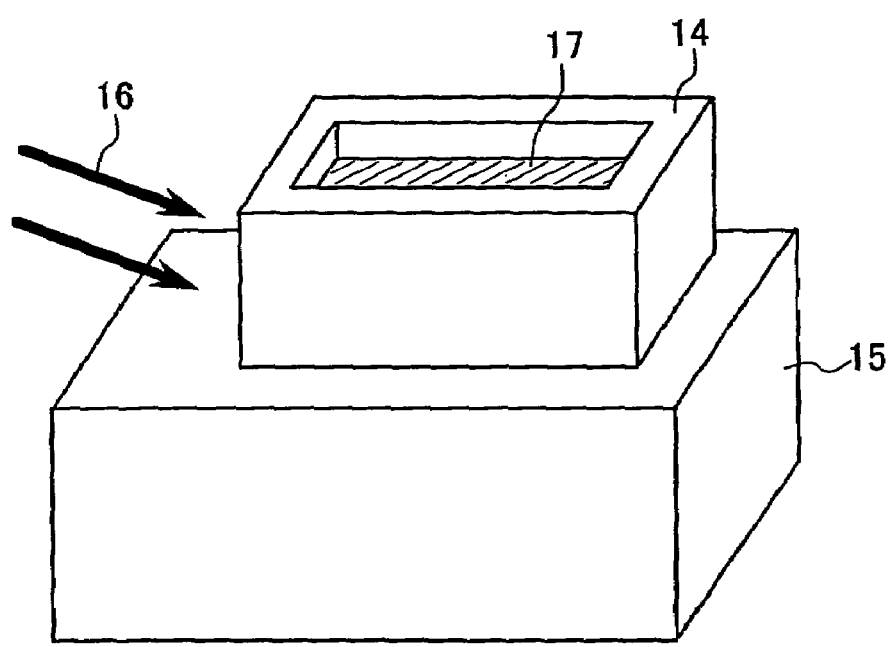
FIG. 3 is a perspective view of the device shown in FIG. 1.

FIGS. 1, 2, and 3 illustrate an example of a basic configuration of a fluorescence detecting device of the present invention. FIG. 1 is a cross-sectional view illustrating a structure of a photodetector part of the foregoing device, and FIG. 3 is a perspective view of the photodetector part of the foregoing device. FIG. 2A is a circuit diagram of a fluorescence detecting circuit of the foregoing device, and FIG. 2B is a driving timing chart of the fluorescence detecting circuit. In FIGS. 1 and 3, the same elements are designated by the same reference numerals.

As shown in FIG. 3, the photodetector part of the foregoing device includes a semiconductor integrated circuit substrate 15 and a fluorescence reaction vessel composed of a transparent container 14, as principal constituent elements. The fluorescence reaction vessel contains a fluorescence reaction solution 17. On the semiconductor integrated circuit substrate 15, a fluorescence detecting circuit is provided. It should be noted that 16 denotes an excitation light entering the fluorescence reaction vessel.

As shown in FIG. 2A, the fluorescence detecting circuit includes a photodiode 22, an amplifying transistor 24 whose gate is fed with a voltage of the photodiode 22, a reset transistor 23 that resets charges of the photodiode 22, and a load transistor 25. In the fluorescence detecting circuit, the amplifying transistor 23 and the load transistor 25 constitute a source follower circuit. It should be noted that, in FIG. 2A, 32 denotes a power source of the amplifying transistor 24, 33 denotes a reset power source of the reset transistor 23, and 34 denotes a timing control input terminal of the reset transistor. 35 denotes a signal output terminal of the source follower circuit composed of the amplifying transistor 24 and the load transistor 25.

The fluorescence detecting circuit operates in the following manner. First of all, a cathode side of the photodiode 22 is charged by the reset transistor 23 so as to have a positive voltage. Here, the source follower circuit composed of the amplifying transistor 24 and the load transistor 25 has a signal output substantially equal to a gate voltage of the amplifying transistor 24. Since the gate of the amplifying transistor 24 is connected with the cathode of the photodiode 22, the signal output terminal 35 has a voltage substantially equal to a voltage of the reset power source 33 upon resetting. In this state, when light is incident on the photodiode 22, electrons are generated by photoelectric conversion. The electrons are accumulated in a n-type impurity layer 8 forming the photodiode 22, thereby lowering the voltage on the cathode side of the photodiode 22. This causes the gate voltage of the amplifying transistor 24 to decrease, thereby causing the voltage of the signal output terminal 35 to decrease also. This sequence of operations can be illustrated by a timing chart as shown in FIG. 2B. More specifically, when a transition to a high level is made at the timing control input terminal 34 of the reset transistor 23 (the transistor is turned on), the signal output terminal 35 is charged so as to have a voltage of the reset power source 33. Thereafter, when a transition to a low level is made at the timing control input terminal 34 of the reset transistor 23 (the transistor is turned off), the photoelectric conversion by the photodiode 22 causes a change in the voltage at the timing control input terminal 34 of the reset transistor 23, and likewise causes a change in the voltage of the signal output terminal 35. The voltage of the signal output terminal 35 indicates an intensity of light subjected to the photoelectric conversion.

FIG. 1 is a cross-sectional view of a photodetector part of the foregoing device. A photodiode, an amplifying transistor, and a reset transistor are formed on this part of the semiconductor integrated circuit substrate 15. As shown in the drawing, the foregoing photodiode is configured so that an n-type impurity layer 8 (second-conductivity-type semiconductor layer) is formed on a surface part of a p-type silicon substrate 7 (low-concentration first-conductivity-type semiconductor layer), and further, a p+-type impurity layer 21 (high-concentration first-conductivity-type semiconductor layer) is formed in a surface portion thereof. The p+ impurity layer 21 composing the photodiode is connected to a constant voltage source. Moreover, the photodiode is connected electrically with the gate 3 of the amplifying transistor 6 via a metal wire 1. 2 and 5 denote a source metal wire and a drain metal wire of the amplifying transistor 6, respectively. The foregoing photodiode is connected electrically with the reset transistor 9. 11 denotes a gate of the reset transistor 9, and 10 denotes a reset power source line. 12 denotes a metal layer that shields elements other than the photodiode (for instance, active elements such as the reset transistor). 4 denotes an interlayer insulation layer. The fluorescence reaction vessel 13 is arranged above the foregoing photodiode.

In the foregoing device, when an excitation light 16 is applied to the fluorescence reaction vessel 13, a part of a fluorescence generated in the fluorescence reaction vessel 13 is incident on the photodiode, where the light is subjected to the photoelectric conversion, whereby signal charges are generated. The signal charges are accumulated in the n-type impurity layer 8, and a voltage according to the foregoing charges is fed to the gate of the amplifying transistor 6. Here, it should be noted that any charges remaining in the photodiode are discharged by the reset transistor before the signal charges are accumulated. Thereafter the photodetector circuit operates as described above, whereby light subjected to the photoelectric conversion is detected.

In the foregoing device, the p+ impurity layer 21 composing the photodiode functions as an excitation-light-entry preventing layer that prevents photodiode are discharged by the reset transistor before the signal charges are accumulated. Thereafter the photodetector circuit operates as described above, whereby light subjected to the photoelectric conversion is detected.

In the foregoing device, the p+ impurity layer 21 composing the photodiode functions as an excitation-light-entry preventing layer that prevents or suppresses the entry of charges generated by the photoelectric conversion of the excitation light into the n-type impurity layer 8. When light enters a material having an optical-absorption coefficient $\alpha$, a charge generation ratio g(d) indicative of a ratio of charges obtained by photoelectric conversion at a depth of d is expressed as $\gamma \cdot \Phi \cdot \alpha \cdot \exp(-\alpha \cdot d)$, where $\gamma$ represents a quantum efficiency, and $\Phi$ represents a flux density. Since the optical-absorption coefficient a of silicon increases as the wavelength decreases in the vicinity of the visible light range, light with a short wavelength tends to be subjected to the photoelectric conversion and absorbed in the vicinity of a surface of the layer. When the excitation light applied thereto for exciting a fluorescence has a wavelength shorter than that of the fluorescence, the excitation light is absorbed in a region closer to the surface than the region where the fluorescence is absorbed. Thus, charges generated by the excitation light are absorbed by the p+ impurity layer 21, thereby resulting in that charges originating from the excitation light, which are unnecessary, hardly are accumulated in the n-type impurity layer 8.

In the foregoing device, the semiconductor integrated circuit substrate 15 is produced by, for instance, the MOS (metal-oxide film-semiconductor) process for producing an integrated circuit (IC) with a silicon substrate 7, but it is not limited to this in the present invention. The semiconductor integrated circuit substrate 15 may be, for instance, a polycrystalline silicon integrated circuit substrate, an amorphous silicon integrated circuit substrate, or a GaAs integrated circuit substrate formed on a glass substrate. Furthermore, the transparent container 14 composing the fluorescence reaction vessel 13 can be made of, for instance, quartz, polymethyl methacrylate (PMMA), etc., but the material is not limited to these. Any material may be used as long as it has a high light transmittance and emits the least possible fluorescence. Furthermore, in the foregoing device, the interlayer insulation film 4, that is, the surface part of the semiconductor integrated circuit substrate 15, preferably is flattened by the chemical machining process (CMP) or the like. In the case where the semiconductor integrated circuit substrate 15 has a flat surface, it is foregoing device is performed, for instance, in the following manner. First of all, a single-strand DNA with the complementary sequence to that of a gene as a target of the detection is fixed in the fluorescence reaction vessel. The fixing method is not limited particularly, and any usual method may be used. A DNA (oligonucleotide) may be synthesized directly on a bottom of the fluorescence reaction vessel, or alternatively, the bottom of the fluorescence reaction vessel may be coated with a material to which a DNA tends to be bound, and a cloned DNA or a PCR product may be fixed thereon. Then, a sample solution is introduced into the fluorescence reaction vessel. Here, in the case where the target DNA itself is labeled with a fluorescent dye such as Cy3, the fluorescence reaction vessel may be washed after the sample solution is introduced. Even in the case where the target DNA is not labeled with a fluorescent dye, a fluorescent intercalator such as SYBR-Green or the like may be put in the sample solution or the fluorescence reaction vessel. Then, the excitation light is projected into the fluorescence reaction vessel, for example, from a side thereof. In the case where the single-strand DNA fixed on the bottom of the fluorescence reaction vessel and the target DNA are hybridized thereby forming a double strand, a fluorescence is emitted radially by either the fluorescent intercalator or the fluorescent label of the target DNA, which has entered in the double strand. In the case where the SYBR-Green is used, a second harmonic generation (SHG) laser with a wavelength of 473 nm may be projected thereto as the excitation light. A part of the fluorescence emitted is detected by the photodiode, and converted by the photoelectric conversion into electric signals. Thereafter, the aforementioned operations are carried out by the semiconductor integrated circuit substrate, whereby electric signals according to the foregoing fluorescence are output.

In the case where the foregoing device is configured so as to include a plurality of photodiodes and single-strand DNAs of a plurality of types are fixed accordingly, a plurality of samples can be analyzed in one detecting operation.

Furthermore, though a single-strand DNA is fixed on the bottom of the fluorescence reaction vessel in the foregoing case described as an example, an antibody or an antigen may be fixed instead. In this case, a sample solution of a fluorescent-labeled antibody or antigen is put in the fluorescence vessel. Thereafter, the sample solution is removed, and the excitation light for fluorescence is projected thereto. Here, in the case where an antigen-antibody complex is formed, a fluorescence is emitted, which is detected by a photodiode. Alternatively, the enzyme immunoassay (ELISA) may be applied. In this case, a first antibody is fixed on the bottom of the fluorescence reaction vessel, to which a sample solution containing an antigen is supplied. Then, an antigen-antibody complex is formed. Further, a second antibody, which is enzyme-labeled, is supplied thereto, so that a complex is formed in a sandwich structure in which the first antibody, the antigen, the second antibody are arranged in the stated order. Then, a substrate that is changed to a fluorescent substance by an enzyme reaction is added thereto, so as to be subjected to an enzyme reaction. The excitation light is projected thereto, and a fluorescence of the fluorescent substance produced is detected by the photodiode. It should be noted that in the fluorescence detection by the antibody-antigen reaction, in the case where a plurality of photodiodes are provided, a plurality of antibodies or antigens may be fixed so that they can be analyzed at once.

Furthermore, in this device, the gene amplification such as the PCR may be performed. In this case, a sample solution containing a target DNA, and a buffer solution containing a pair of primers that can be hybridized with both ends of the target DNA, a heat-resistant DNA polymerase (TaqDNA polymerase, etc.), dNTPs, a fluorescent intercalator, and the like are put in the foregoing fluorescence reaction vessel. Then, by repeating a series of steps of the denaturation of the target DNA with heat, the annealing of the primers, and the elongation of the DNA polymerase, the target DNA is amplified. Since the fluorescent intercalator is bound to an amplification product obtained, irradiation with the excitation light causes a fluorescence to be emitted, which can be detected by the photodiode.

Second Embodiment

Figure 4:
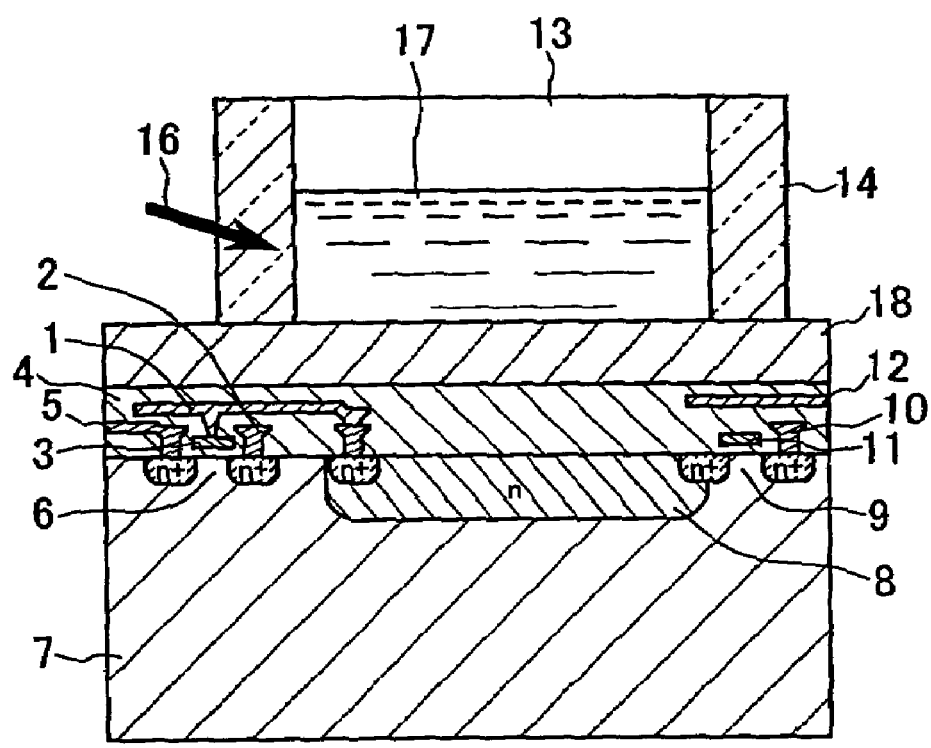
FIG. 4 is a cross-sectional view illustrating another example of the first fluorescence detecting device of the present invention.

FIG. 4 is a cross-sectional view illustrating another example of the fluorescence detecting device of the present invention. In the drawing, the same elements as those in FIG. 1 are designated by the same reference numerals.

The device includes a filter layer 18 that absorbs or reflects an excitation light. The filter layer 18 is provided between the n-type impurity layer 8 and a bottom of the fluorescence reaction vessel 13. As a material of the filter layer 18, any material may be used as long as it transmits a fluorescence but hardly transmits the excitation light 16. For instance, a pigment film, a multilayer interference film, a dyed film, a colored glass, etc. may be used. For instance, in the case where the excitation light has a wavelength of 497 nm and the fluorescence has a wavelength of 520 nm, a pigment film that absorbs light with a wavelength of not more than 510 nm may be used as the filter layer 18. In the case where a multilayer interference film is used as the filter layer 18, the filter layer can be formed by producing a semiconductor integrated circuit substrate and laminating materials having different refractive indices from each other on the surface of the board so as to form a multilayer film. This multilayer film can be formed by laminating silicon dioxide and titanium oxide, or alternatively, silicon dioxide and silicon nitride, by sputtering or chemical vapor deposition (CVD).

Furthermore, by measuring the light transmission spectral characteristics of the filter layer 18 and the spectral characteristics of the fluorescence and the excitation light beforehand, it is possible to calculate a ratio between the transmittance of the filter layer with respect to the fluorescence and the transmittance of the filter layer with respect to the excitation light. With such a transmittance ratio determined, it is possible to calculate a more accurate fluorescence intensity based on the value (light intensity) measured by the foregoing device and the foregoing ratio.

The other configurations, conditions, operations, etc. of this device are identical to those in the first embodiment described above.

Third Embodiment

Figure 5:
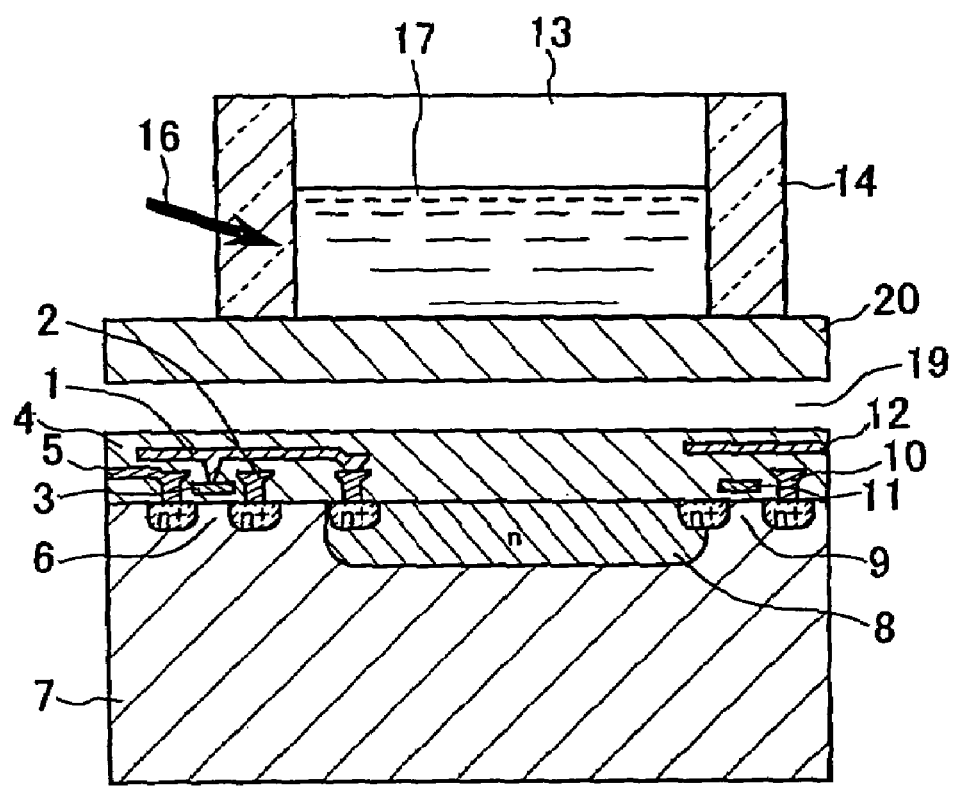
FIG. 5 is a cross-sectional view illustrating still another example of the first fluorescence detecting device of the present invention.

FIG. 5 is a cross-sectional view illustrating still another example of the fluorescence detecting device of the present invention. In the drawing, the same elements as those in FIG. 1 are designated by the same reference numerals.

This device is configured so as to include a transparent layer 20 made of quartz glass on a bottom face of the fluorescence reaction vessel 13, and a space between the transparent layer 20 and the n-type impurity layer 8. In this space between the transparent layer 20 and the n-type impurity layer 8, a gas, for instance, air, is present, thereby forming a gas layer 19. Since the air has a refractive index of 1.0 and the quartz glass has a refractive index of 1.5, the refractive index decreases at an interface between the transparent layer 20 and the gas layer 19, thereby causing light entering from the quartz glass layer 20 to the gas layer 19 to be reflected totally, provided that the light has an incident angle of not less than approximately 44° with respect to a normal direction. Therefore, in the case where the excitation light 16 is caused to be incident thereon, for instance, with an incident angle of 60° with respect to the normal direction, the excitation light is reflected at the interface between the transparent layer 20 and the gas layer 19, thereby not entering the n-type impurity layer 8. Therefore, it is possible to cause only the fluorescence to enter the n-type impurity layer 8.

The gas layer 19 is not limited to the air layer, but any may be used as long as it has a suitably small refractive index. For instance, the gas layer may be a nitrogen layer, or a vacuum layer. Besides, the material forming the transparent layer 20 is not limited to quartz glass, but any transparent material that transmits a fluorescence and has a refractive index higher than that of the gas layer 19 may be used. For instance, polymethyl methacrylate, non-fluorescent glass, etc. may be used.

The other configurations, conditions, operations, etc. of the foregoing device are identical to those in the first embodiment described above.

Fourth Embodiment

Figure 6:
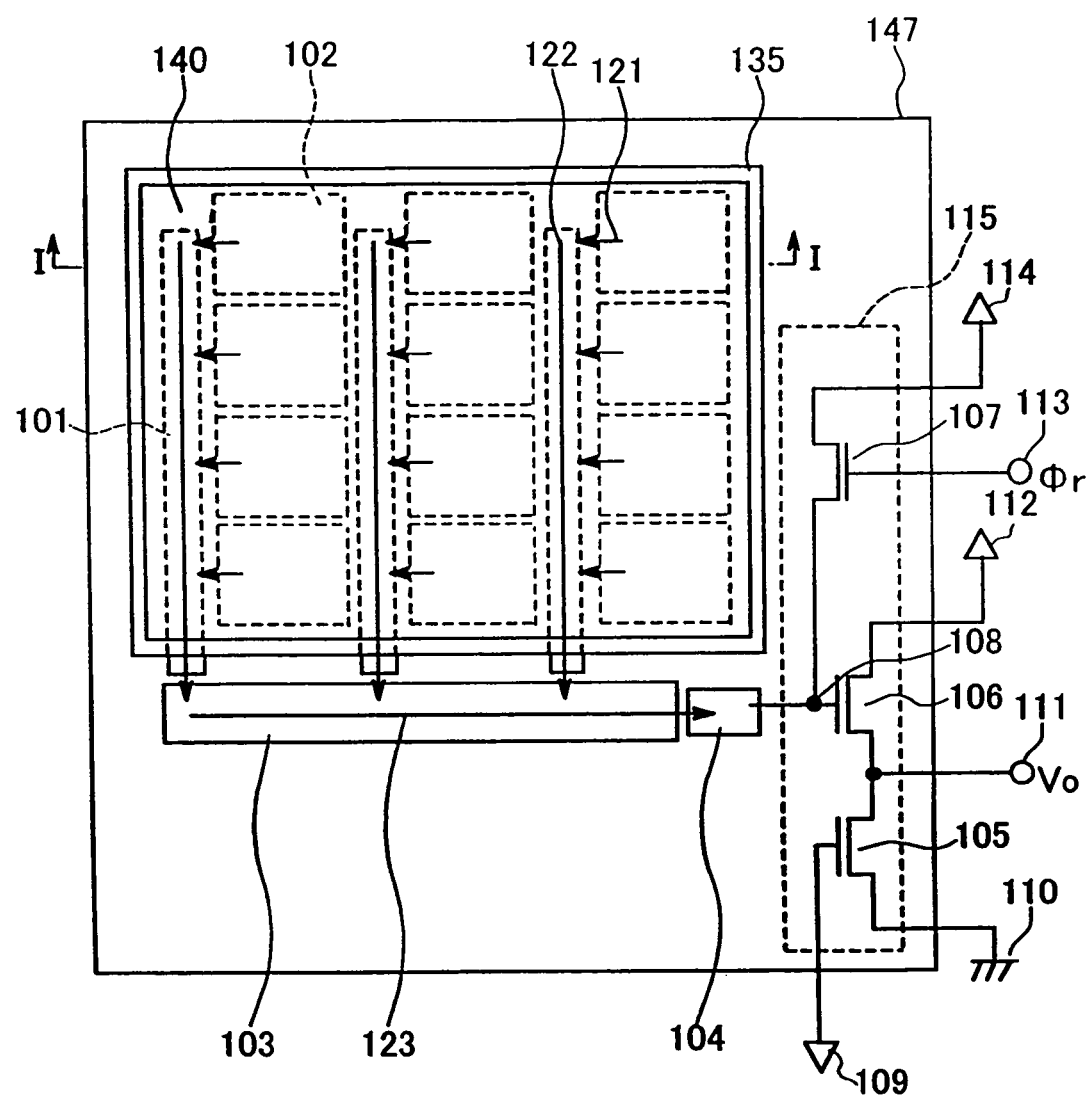
FIG. 6 is a circuit diagram illustrating still another example of the first fluorescence detecting device of the present invention.
Figure 7:
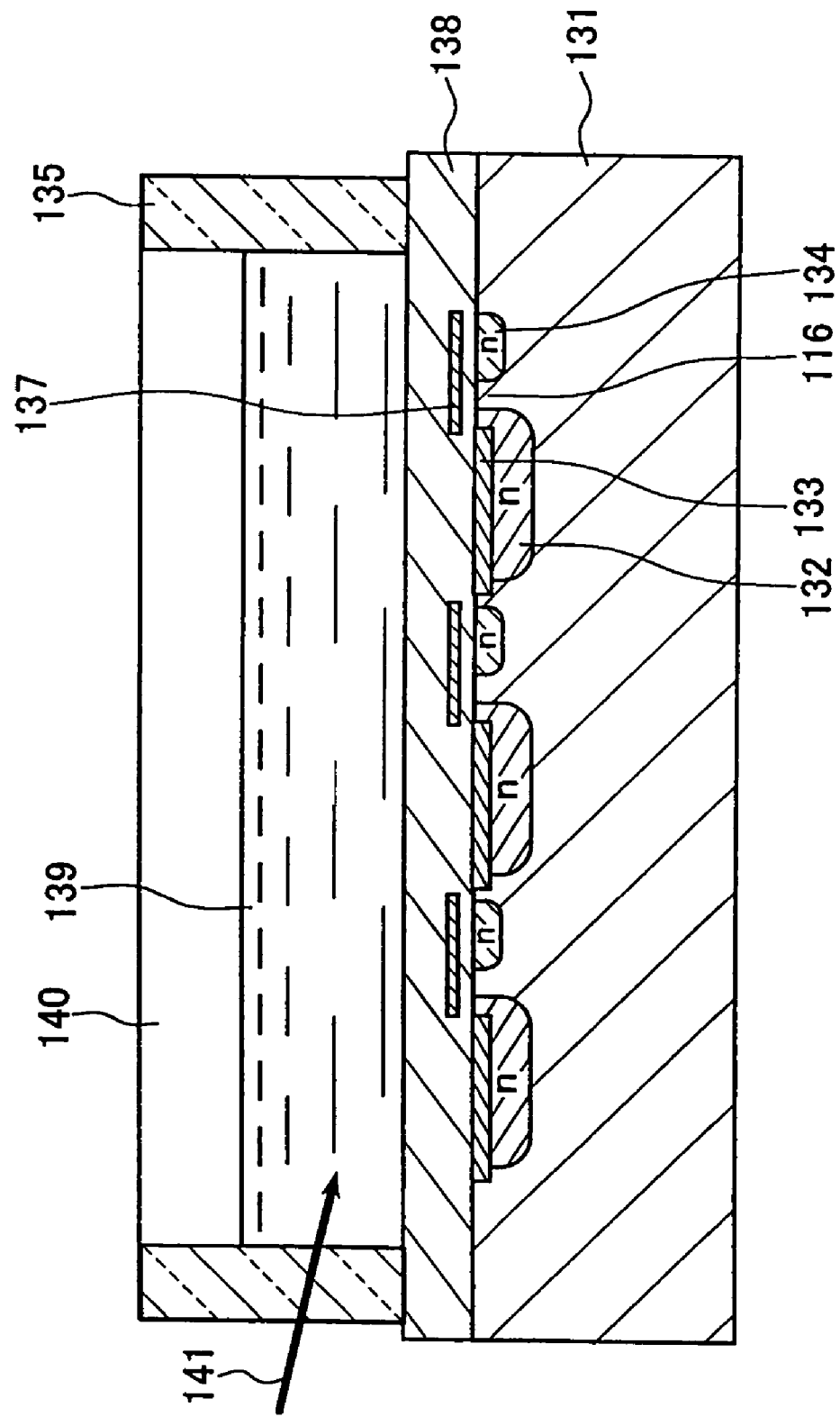
FIG. 7 is a cross-sectional view of the device shown in FIG. 6, which is taken along a line I—I shown therein.

FIG. 6 is a plan view illustrating still another example of the fluorescence detecting device of the present invention. FIG. 7 is a cross-sectional view of the device taken in a line I—I direction shown in FIG. 6. In these drawings, the same elements are designated by the same reference numerals.

As shown in FIG. 6, a photodetector part of the foregoing device includes a semiconductor integrated circuit substrate 147 and a transparent container 135 composing a fluorescence reaction vessel 140 made of a transparent material as principal constituent elements. The foregoing fluorescence reaction vessel 140 contains a fluorescence reaction solution. On the foregoing semiconductor integrated circuit substrate 147, there are formed a plurality of photodiodes 102 arrayed two-dimensionally, a Y transfer section 101, an X transfer section 103, a charge accumulating section 104, and an amplifying circuit 115. The Y transfer section 101 and the X transfer section 103 are so-called charge coupled devices (CCD), each of which has a plurality of transfer electrodes arrayed in a transfer direction. The amplifying circuit 115 is a signal detecting circuit for detecting charges accumulated in the charge accumulating section 104, and includes an amplifying transistor 106 whose gate is fed with a voltage of the charge accumulating section 104, a reset transistor 107 that resets charges of the charge accumulating section 104, and a load transistor 105. In the amplifying circuit 115, the amplifying transistor 106 and the load transistor 105 constitute a source follower circuit. It should be noted that in FIG. 6, 108 denotes a gate of the amplifying transistor 106, 114 denotes a reset power source, 113 denotes a reset pulse (r) terminal, 109 denotes a gate power source of the load transistor, 112 denotes a power source of the source follower circuit, 110 denotes a ground power source, and 111 denotes a signal output terminal.

When an excitation light 141 is applied to the fluorescence reaction vessel 140 a fluorescence is generated, and when the fluorescence enters the photodiodes 102, it is subjected to the photoelectric conversion, whereby charges are accumulated therein. The charges thus obtained by the photoelectric conversion and accumulated are moved to the Y transfer section 101 by a readout operation 121. The charges moved to the Y transfer section 101 are transferred to the X transfer section 103 by a transfer operation 122 of applying a pulse voltage to a plurality of transfer electrodes of the Y transfer section 101. Then, the charges transferred to the X transfer section 103 are transferred to the charge accumulating section 104 by a transfer operation 123 of applying a pulse voltage to a plurality of transfer electrodes of the X transfer section 103. Through these operations, the charges obtained by the photoelectric conversion by the photodiodes 102 are accumulated in the charge accumulating section 104.

The following will describe an operation performed by the amplifying circuit 115. Before charges are accumulated in the charge accumulating section 104, a pulse that turns on the reset transistor 107 is fed from the reset pulse terminal 113 to a gate of the reset transistor 107, so that the charge accumulating section 104 is charged to have a voltage of the reset power source 114. This reset operation causes the charge accumulating section 104 to have a voltage of the reset power source 114. Thereafter, the charges generated by the photoelectric conversion of the fluorescence are accumulated in the charge accumulating section 104, thereby causing a change in the voltage of the charge accumulating section 104. The charge accumulating section 104 is connected with the gate 118 of the amplifying transistor 106, and hence, the gate 118 has a voltage equal to that of the charge accumulating section 104. Since the amplifying transistor 106 and the load transistor 105 composes a source follower circuit, the signal output terminal 111 (Vo) has a voltage that is substantially equal to the voltage of the gate 118. With this voltage of the signal output terminal 111 (Vo), an intensity of the fluorescence can be determined. In other words, when the fluorescence is intense, charges obtained by the photoelectric conversion increase, thereby lowering the voltage of the charge accumulating section 104. Consequently, the voltage of the signal output terminal 111 (Vo) drops. When the fluorescence is weak, charges Since the amplifying transistor 106 and the load transistor 105 composes a source follower circuit, the signal output terminal 111 (Vo) has a voltage that is substantially equal to the voltage of the gate 118. With this voltage of the signal output terminal 111 (Vo), an intensity of the fluorescence can be determined. In other words, when the fluorescence is intense, charges obtained by the photoelectric conversion increase, thereby lowering the voltage of the charge accumulating section 104. Consequently, the voltage of the signal output terminal 111 (Vo) drops. When the fluorescence is weak, charges obtained by the photoelectric conversion decrease, thereby causing the voltage of the signal output terminal 111 (Vo) to approximate a voltage of the reset power source 114, which is a high voltage.

As shown in FIG. 7, in the foregoing device, a photodiode is composed of a p-type semiconductor substrate 131 (low-concentration first-conductivity-type semiconductor layer), a n-type impurity layer 132 (second-conductivity-type semiconductor layer), and a p+ impurity layer 133 (high-concentration first-conductive-type semiconductor layer), so that the same mechanism as that in the first embodiment eliminates influences of the excitation light.

Furthermore, the foregoing device includes readout transistors 116 for reading out charges generated by the photoelectric conversion, n-type impurity layers 134 that serve as channels of the Y transfer section 101, an interlayer insulation film 138, polysilicon layers 137, shielding metal layers 137, and a transparent container 135 composing a fluorescence reaction vessel 140. The polysilicon layers 137 serve as transfer electrodes of the Y transfer section 101, as well as gates of the readout transistor 116. The fluorescence from the fluorescence reaction solution 139 is subjected to the photoelectric conversion at the photodiode, and signal charges generated therein are accumulated in the n-type impurity layer 132 of each photodiode. It should be noted that before accumulating the signal charges, the n-type impurity layers 132 are depleted. Then, a high voltage is applied to the polysilicon layers 137 so as to move the charges accumulated in the n-type impurity layers 132 to the n-type impurity layers 134 of the Y transfer section 101. This operation is equivalent to the readout operation 121 shown in FIG. 6.

Figure 8:
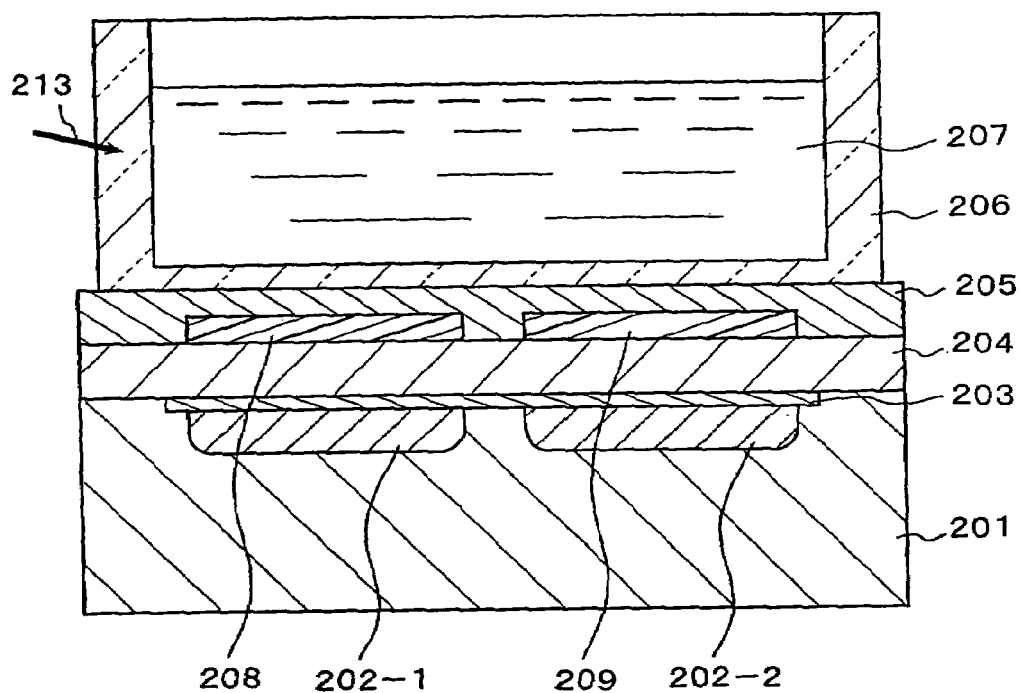
FIG. 8 is a cross-sectional view illustrating an example of a second fluorescence detecting device of the present invention.
Figure 10:
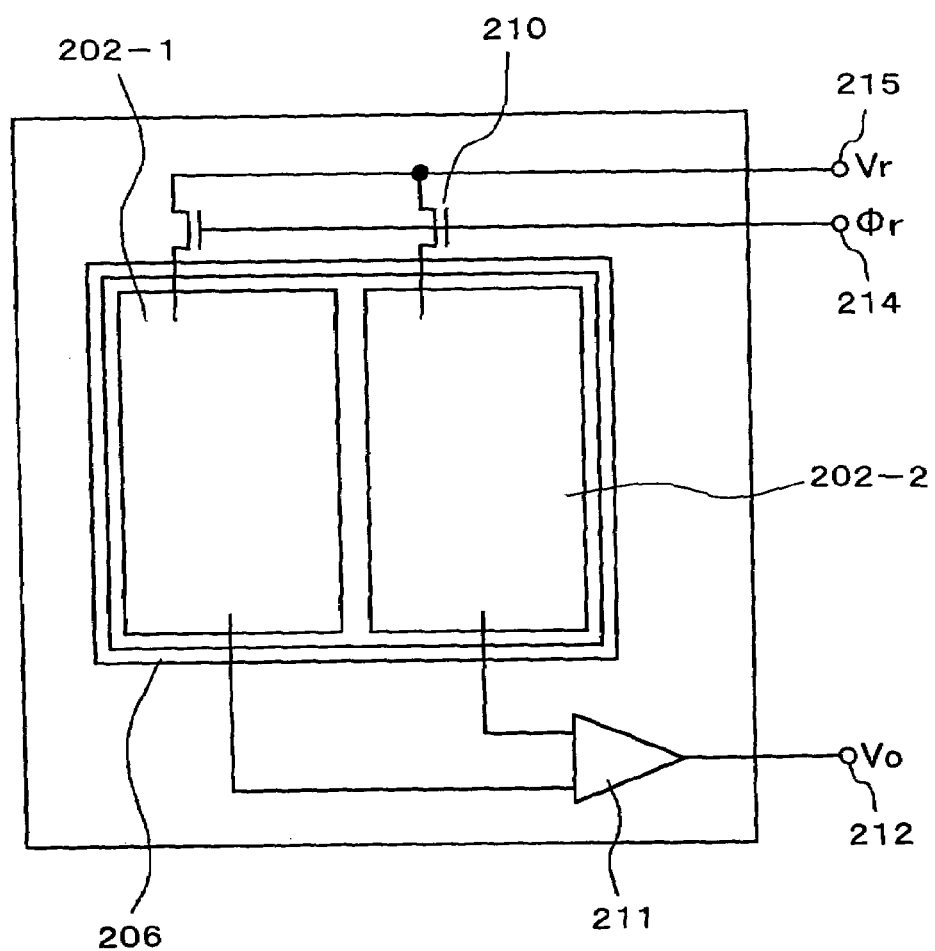
FIG. 10 is a perspective view of the device shown in FIG. 8.
Figure 11:
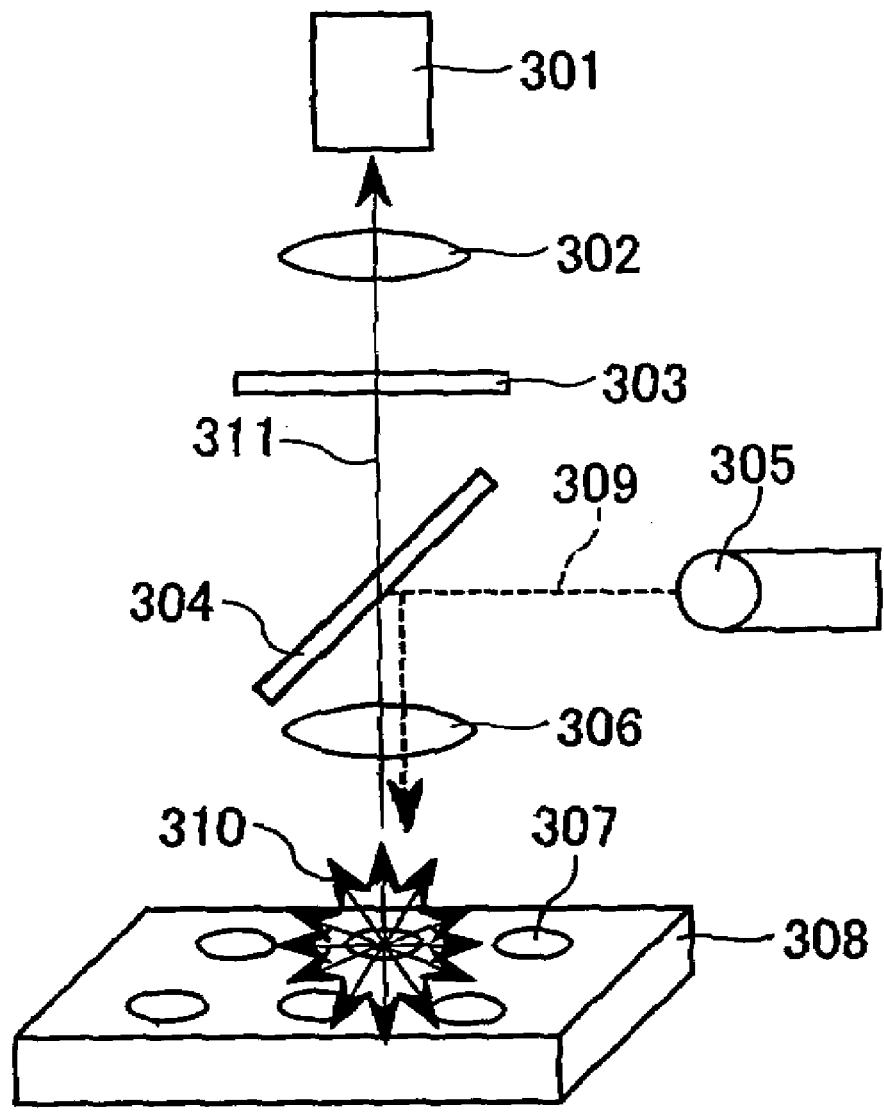
FIG. 11 is a view illustrating a configuration of a conventional fluorescence detecting device.

Thus, an effect of the suppression of influences of charges originating from the excitation light can be achieved also by transferring signals charges from the photodiode to an accumulation capacitor such as a charge coupled device (CCD) temporarily, and thereafter feeding the same to the amplifying circuit (signal detecting circuit). detecting device of the present invention. FIG. 8 is a cross-sectional view illustrating a structure of a photodetector portion of the foregoing device, and FIG. 10 is a plan view illustrating the photodetector portion of the device. In the foregoing drawings, the same elements are designated by the same reference numerals.

As shown in the drawings, the photodetector portion of the device includes a semiconductor integrated circuit substrate, first and second optical filters 208 and 209 that have different light transmission spectral characteristics from each other, and a fluorescence reaction vessel 206 made of a transparent material, as principal constituent elements. The fluorescence reaction vessel 206 contains a fluorescence reaction solution 207 containing a fluorescent material. Furthermore, a fluorescence detecting circuit is formed on the semiconductor integrated circuit substrate. It should be noted that 213 denotes an excitation light incident on the fluorescence reaction vessel 206.

As shown in FIG. 10, the fluorescence detecting circuit includes two photodiodes 202-1 and 202-2, an amplifying circuit 211 to which signals from the photodiodes are supplied, and reset transistors 210 that reset signals of the photodiodes (put the photodiodes in a reversely biased state). The amplifying circuit 211 performs a specific calculation with signals supplied from the photodiodes, and outputs, as a result of the calculation, a signal according to a fluorescence, from which influences of the excitation light have been eliminated. The calculation will be described later. It should be noted that in FIG. 10, 212 denotes a signal output terminal of the amplifying circuit 211, 214 denotes a reset pulse terminal, and 215 denotes a reset power source of the reset transistors 210.

FIG. 8 is a cross-sectional view of the photodetector portion of the foregoing device. Two n-type impurity layers 202-1 and 202-2 are formed on a p-type silicon substrate 201, and a high-concentration p-type impurity layer 203 is formed thereon, whereby two photodiodes (first and second photodiodes) are formed. On the two photodiodes, a green-color filter 208 (first optical filter) and a blue-color filter 209 (second optical filter) are arranged, respectively, with an interlayer film and a passivation film 204 interposed therebetween. Furthermore, a fluorescence reaction vessel 206 is formed thereon, with a transparent flattening film 205 interposed therebetween. The foregoing filters are color filters containing pigments. Furthermore, as described above, the fluorescence reaction vessel 206 contains the fluorescence reaction solution 207. In this device, the p-type silicon substrate 201 and the high-concentration p-type impurity layer 203 are grounded. While the device operates, the photodiodes are put in a reversely biased state before a fluorescence is subjected to the photoelectric conversion as will be described later. Accordingly, the impurity concentration of the high-concentration p-type impurity layer 203 is set so that the layer is not depleted completely even when the photodiodes are put in the reversely biased state.

In the device according to the present embodiment also, as in the first embodiment, the semiconductor integrated circuit substrate can be made of, for instance, a silicon substrate, but it is not limited to this in the present invention. The semiconductor integrated circuit substrate may be, for instance, a polycrystalline silicon integrated circuit substrate, an amorphous silicon integrated circuit substrate, or a GaAs integrated circuit substrate formed on a glass substrate. In this device also, the semiconductor integrated circuit substrate preferably has a flattened surface. Besides, the fluorescence reaction vessel can be formed by arranging a transparent container on a semiconductor integrated circuit substrate, as shown in the drawing. The transparent container may be made of, for instance, quartz, or polymethyl methacrylate (PMMA), but the material is not limited to these. Any material may be used as long as it has a high light transmittance and emits the least possible fluorescence.

The following will describe an operation of the foregoing device. First of all, a pulse is supplied to the reset pulse terminal 214, to turn on the reset transistors 210, thereby charging the n-type impurity layers 202-1 and 202-2 of the photodiodes so that they have positive voltages. This operation puts the photodiodes in the reversely biased state.

Then, the reset transistors 210 are turned off, and detection of a fluorescence is carried out. When an excitation light 213 is applied to the fluorescence reaction vessel 206, a part of a fluorescence generated in the fluorescence reaction vessel 206 is incident on the photodiodes, where the light is subjected to the photoelectric conversion, whereby signal charges are generated. The signal charges are accumulated in the n-type impurity layers 202-1 and 202-2, and electric signals according to the foregoing charges are fed to the amplifying transistor 211. Here, a signal from the photodiode 213-1 and a signal from the photodiode 213-2 are supplied to the amplifying circuit 211, and a fluorescence intensity is calculated based on these signals.

Figure 9A:
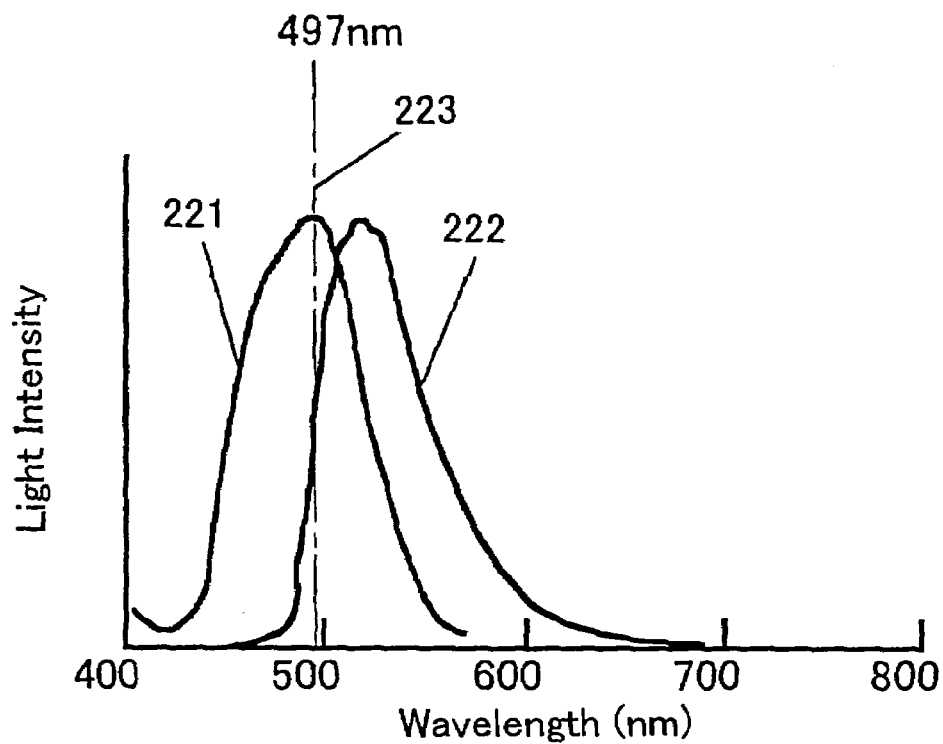
FIG. 9A is a graph illustrating spectral characteristics of an absorbed light and a fluorescence of a fluorescent material.
Figure 9B:
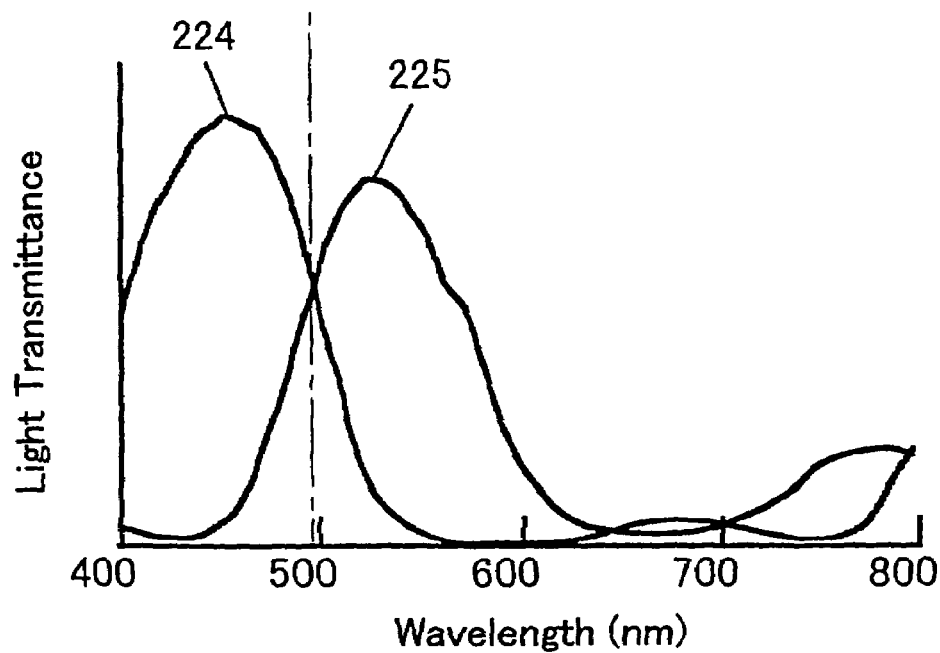
FIG. 9B is a graph illustrating light transmission spectral characteristics of optical filters.

The detection of a fluorescence will be described in more detail below, by taking as an example a case where a light with an absorption peak wavelength of 497 nm, which provides the highest fluorescence efficiency, is employed as an excitation light, and SYBR-Green I (intercalator) is employed as a fluorescent. FIG. 9A shows a light absorption spectral characteristic 221 and a fluorescence spectral characteristic 222 of SYBR-Green I (fluorescent). 223 indicates a position of the excitation light wavelength of 497 nm in the graph. As shown in the drawing, the fluorescence has an emission peak on a long wavelength side as compared with a light absorption peak thereof. On the photodiodes, the excitation light and the fluorescence are incident after having passed through the green-color filter 208 or the blue-color filter 209. FIG. 9B shows a transmission spectral characteristic 225 of the green-color filter and a transmission spectral characteristic 224 of the blue-color filter. The difference between the excitation light and the fluorescence in the spectral characteristics as shown in FIG. 9A and the difference between the filters in the spectral characteristics as shown in FIG. 9B make the signal from the n-type impurity layer 202-1 under the green-color filter 208 and the signal from the n-type impurity layer 202-2 under the blue-color filter 209 different from each other. Since the green-color filter 208 has a light transmission peak close to the peak wavelength of the fluorescence, the photodiode including the n-type impurity layer 202-1 performs more efficient photoelectric conversion with respect to the fluorescence than with respect to the excitation light. In contrast, since the blue-color filter 209 has a light transmission peak far from the peak wavelength of the fluorescence, the photodiode including the n-type impurity layer 202-2 performs more efficient photoelectric conversion with respect to the excitation light than with respect to fluorescence. A ratio between a light transmittance with respect to the excitation light and a light transmittance with respect to the fluorescence can be determined beforehand as to each of the green-color filter 208 and the blue-color filter 209, based on the spectral characteristics of the excitation light and the fluorescence. According to the ratios of light transmittances thereof and the signals from the n-type impurity layers 202-1 and 202-2, a fluorescence intensity can be calculated. In this case, since the green-color filter 208 efficiently transmits the fluorescence, the measurement with a high-sensitivity can be achieved.

One example of the foregoing calculation is shown, with reference to FIGS. 9A and 9B. For instance, it is assumed that in the case where a fluorescence is obtained with an excitation with a wavelength of not more than 497 nm, a light having passed through a filter with the spectral characteristic 225 has an intensity of I1 and includes an excitation light component and a fluorescence component at a ratio of 1:2, and a light having passed through a filter with the spectral characteristic 224 has an intensity of I2 and includes an excitation light component and a fluorescence component at a ratio of 2:1. In this case, the fluorescence intensity can be determined by the following arithmetic expression:

Fluorescence Intensity=$\frac{2}{3}(I1-I2/2)$

To determine an intensity of the fluorescence with an excellent precision with the foregoing calculation, it is desirable that the fluorescence content is small in the light having passed through the filter with the spectral characteristic 224.

It should be noted the filters do not necessarily have the spectral characteristics as shown in FIG. 9B, and two or more types of filters that differ in the transmission peak wavelength and the distribution form will suffice. For instance, a peak wavelength of transmission light passing through one of the filters is set close to a peak wavelength of a fluorescence so that the filter efficiently transmits the fluorescence, and does not transmit much of the excitation light. Here, the other filter is made to have a distribution characteristic so as to include a larger proportion of the excitation light component. The difference between the peak wavelengths of the two filters preferably is greater than a difference between those of the excitation light and the fluorescence. Besides, a half width of the distribution of each of the filters preferably is small; more preferably, it is smaller than a difference between the wavelengths of the excitation light and the fluorescence. The filters having different light transmission spectral characteristics are not limited to the pigment color filters. For instance, interference filters, dyed filters, or colored glass can be used as the foregoing filters.

It should be noted that an operation of the foregoing device for detecting a fluorescence of a gene can be performed in the same manner as that in the first embodiment.

Furthermore, as described above, it is preferable that a plurality of detection units are provided, each of which is composed of the first photodiode and the first optical filter, plus the second photodiode and the second optical filter. This configuration allows the detection units to perform different tests, respectively. For instance, by providing a plurality of the detection units and fixing a plurality of types of single-strand DNAs in the detection units accordingly, a plurality of tests can be carried out with one fluorescence detection.

The invention may be embodied in other forms without departing from the spirit or essential characteristics thereof The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A fluorescence detecting device comprising:
   a semiconductor integrated circuit substrate including a plurality of photodiodes and a signal detecting circuit for detecting charges obtained as a result of photoelectric conversion by the plurality of photodiodes; and
   a fluorescence reaction vessel where a fluorescence reaction occurs, the fluorescence reaction vessel being formed on the plurality of the photodiodes, with a plurality of photodiodes provided per one fluorescence reaction vessel;
   wherein the fluorescence reaction in the one fluorescence reaction vessel generates fluorescence that enters the plurality of photodiodes and is subjected to the photoelectric conversion, and
   wherein an excitation-light-entry preventing layer is formed at either or both of a surface portion of the plurality of photodiodes and a position between the plurality of photodiodes and the fluorescence reaction vessel;
   wherein the photodiodes include a high concentration first-conductivity-type semiconductor layer, a second-conductivity-type semiconductor layer, and a low-concentration first-conductivity-type semiconductor layer that are laminated in the stated order from a surface side of the photodiodes, wherein
   when a reverse bias is applied, a part of the high-concentration first-conductivity- type semiconductor layer is not depleted, and the second-conductivity-type semiconductor layer is depleted, and
   the high-concentration first-conductivity-type semiconductor layer constitutes the excitation-light-entry preventing layer.

2. The device according to claim 1, wherein the excitation-light-entry preventing layer is a light absorbing layer that absorbs an excitation light, and is arranged between the photodiodes and the fluorescence reaction vessel.

3. The device according to claim 1, wherein the excitation-light-entry preventing layer is a light interference layer that reflects an excitation light, and is arranged between the photodiodes and the fluorescence reaction vessel.

4. The device according to claim 1, wherein
   the excitation-light-entry preventing layer is a gas layer, and is arranged between the photodiodes and the fluorescence reaction vessel, and
   an excitation light is set so as to be incident in a direction such that the excitation light is reflected totally at an interface between the gas layer and a bottom face of die fluorescence reaction vessel.

5. The device according to claim 1, wherein a single-strand DNA is fixed on an internal bottom face of the fluorescence reaction vessel.

6. The device according to claim 1, wherein at least one selected from an antibody and an antigen is fixed on an internal bottom face of the fluorescence reaction vessel.

7. A fluorescence detecting method employing the fluorescence detecting device according to claim 1, the method comprising:
   causing excitation light to enter the fluorescence reaction vessel; and
   detecting a fluorescence generated as a result of the entry of the excitation light by means of the photodiodes.

8. The device according to claim 1, wherein signal charges generated in the plurality of photodiodes arc accumulated, and the accumulated charge is measured to detect fluorescence.

* * * * *

UNITED STATES PATENT AND TRADEMARK OFFICE
CERTIFICATE OF CORRECTION

PATENT NO. : 6,995,386 B2 Page 1 of 1
APPLICATION NO. : 10/962239
DATED : February 7, 2006
INVENTOR(S) : Emoto It is certified that error appears in the above-identified patent and that said Letters Patent is hereby corrected as shown below:

On the title page item (54), and col. 1, line 1, "FLUORESCENCE DETECTING DEVICE WITH INTEGRATED CIRCUIT AND PHOTODIODE, AND DETECTION METHOD," should read --FLUORESCENCE DETECTING DEVICE--

Col. 14, line 47: "face of die" should read --face of the--

Signed and Sealed this

Twenty-first Day of November, 2006

JON W. DUDAS
*Director of the United States Patent and Trademark Office*